(12) United States Patent
Rajan et al.

(10) Patent No.: US 6,838,292 B1
(45) Date of Patent: Jan. 4, 2005

(54) DETECTION OF BIOLOGICAL WARFARE AGENTS

(75) Inventors: Krishnaswamy S. Rajan, Elmhurst, IL (US); Stephen S. Mainer, Crest Hill, IL (US)

(73) Assignee: Alion Science and Technology Corporation, McLean, VA (US)

( * ) Notice: Subject to any disclaimer, the term of this patent is extended or adjusted under 35 U.S.C. 154(b) by 0 days.

(21) Appl. No.: 09/549,353

(22) Filed: Apr. 14, 2000

Related U.S. Application Data (60) Provisional application No. 60/130,009, filed on Apr. 19, 1999.

(51) Int. Cl.$^7$ ..................... G01N 33/53; G01N 33/543
(52) U.S. Cl. ..................... 436/518; 436/528; 435/4; 435/6; 435/7.1; 435/34; 435/36; 435/39; 435/242; 435/287.1; 422/68.1; 422/82.05; 422/82.08; 340/506; 340/513; 340/557
(58) Field of Search ..................... 436/172, 518, 436/528; 435/7.1, 6, 36, 39, 4, 34, 242, 287.1; 422/82.05, 82.08, 68.1; 340/506, 513, 557

(56) References Cited

U.S. PATENT DOCUMENTS

| | | | |
|---|---|---|---|
| 4,256,834 A | | 3/1981 | Zuk et al. ..................... 435/7 |
| 4,565,790 A | | 1/1986 | Hemmila et al. ........... 436/537 |
| 4,868,103 A | | 9/1989 | Stavrianopoulos et al. ..... 435/5 |
| 5,005,005 A | * | 4/1991 | Brossia et al. ............... 340/604 |
| 5,019,518 A | * | 5/1991 | Diehl et al. .................. 436/172 |
| 5,082,630 A | * | 1/1992 | Partin et al. .................. 422/83 |
| 5,124,268 A | | 6/1992 | Dakubu ...................... 436/537 |
| 5,190,729 A | * | 3/1993 | Hauenstein et al. .......... 422/91 |
| 5,262,299 A | | 11/1993 | Evangelista et al. .......... 435/6 |
| 5,328,847 A | | 7/1994 | Case et al. ................... 435/291 |
| 5,474,910 A | * | 12/1995 | Alfano ......................... 435/34 |
| 5,545,834 A | | 8/1996 | Singh et al. ................... 544/6 |
| 5,599,923 A | | 2/1997 | Sessler et al. ............... 540/145 |
| 5,618,732 A | | 4/1997 | Pease et al. ................... 436/8 |
| 5,637,467 A | | 6/1997 | Meltzer ...................... 435/7.9 |
| 5,637,509 A | | 6/1997 | Hemmila et al. ........... 436/537 |

(List continued on next page.)

FOREIGN PATENT DOCUMENTS

| | | | | |
|---|---|---|---|---|
| WO | 9631775 | * | 10/1996 | ................. 33/543 |

OTHER PUBLICATIONS

David Rosen Anal. Chem. 1997 69 1082–1085.*
Dickson et al Journal of Photochemistry and Photobiology B: Biology 27 (1995) 3–19.*

(List continued on next page.)

*Primary Examiner*—Long V. Le
*Assistant Examiner*—Kartic Padmanabhan
(74) *Attorney, Agent, or Firm*—Staas & Halsey LLP (57) ABSTRACT

Methods and devices are provided for the detection of bacterial agents such agents as *Bacillus anthracis* and *Clostridium botulinum* with high sensitivity and selectivity. More specifically, methods and devices are based on a phosphorescence-emission detection system using chelate-stabilized lanthanides (e.g, Eu(III), Tb(III), and Sm(III)) to detect various spore-specific small organic molecules (e.g., dipicolinic acid, diaminopimelic acid, n-acetylmuramic acid, and the like). By careful selection of the chelating agent or ligand coordinated to the lanthanide, both high specificity and selectivity can be obtained. Examples of suitable and preferred sensor systems include N-(2-hydroxyethyl)ethylenediaminetriacetic acid (HEDTA) and N-(2-hydroxyethyl)iminodiacetic acid (HEIDA) combined with europium (III) and/or terbium (III). The chelate-stabilized lanthanides react with the spore-specific "target" molecules to form a characteristically phosphorescent product which can then be detected.

20 Claims, 3 Drawing Sheets

U.S. PATENT DOCUMENTS

| | | | | |
|---|---|---|---|---|
| 5,656,433 A | * | 8/1997 | Selvin et al. | 435/6 |
| 5,672,478 A | * | 9/1997 | Singh et al. | 435/6 |
| 5,736,410 A | * | 4/1998 | Zarling et al. | 436/172 |
| 5,762,873 A | | 6/1998 | Fanning et al. | 422/65 |
| 5,766,956 A | | 6/1998 | Groger et al. | 436/164 |
| 5,798,085 A | | 8/1998 | Seaton et al. | 422/65 |
| 5,876,960 A | * | 3/1999 | Rosen | 435/39 |
| 6,030,840 A | * | 2/2000 | Mullinax et al. | 436/82 |

OTHER PUBLICATIONS

Redkar et al., "Rapid Detection of Select Pathogenic Bacteria by Real Time PCR", Abstract, Scientific Conference on Chemical and Biological Defense Research, Aberdeen Proving Ground (1998).

Ibrahim, "Detection of Biological Agents Using Probe–Based PCR Assay", Abstract, Scientific Conference on Chemical and Biological Defense Research, Aberdeen Proving Ground (1998).

Gatto–Menking et al., "Rapid Post PCR Protection Using IGEN's Origen Analyzer", Abstract, Scientific Conference on Chemical and Biological Defense Research, Aberdeen Proving Ground (1998).

Bruno et al., "Development of Selex DNA Aptamers for the Detection of Anthrax Spores", Abstract, Scientific Conference on Chemical and Biological Defense Research, Aberdeen Proving Ground (1998).

Nagata et al., "Development of Enzyme–linked Immunosorbent Assay (ELISA) to Anthrax for the Persian Gulf", Defense Information System Agency, ADA 297350 (1995).

Bartoszcze et al., "The Sensitivity of the Bioluminescence Method Regarding Microbiological Detection in Contaminated Water and on Surfaces", Abstract, Scientific Conference on Chemical and Biological Defense Research, Aberdeen Proving Ground (1998).

Heraeus, "Fiberlight—Deuterium Light Source Solution for Hand–Held Spectroscopy", brochure.

Whitney, Margarget A., "Lasers Make Rails Safer for Travel", *Photonics Spectra,* Apr. 1999, p. 44.

Grecz, N., et al., "Relation of Metal Chelate Stability to Heat Resistance of Bacterial Spores", *SPORES V,* © 1972 American Society for Microbiology.

Rajan, K. S., et al., "Role of Chelation and Water Binding of Calcium in Dormancy and Heat Resistance of Bacterial Endospores", *Bioinorganic Chemistry,* 8, 477–491 (1978).

* cited by examiner

DETECTION OF BIOLOGICAL WARFARE AGENTS

RELATED APPLICATION

This application is based on, and claims benefit of, U.S. Provisional Application Ser. No. 60/130,009 filed on Apr. 19, 1999.

GOVERNMENT INTEREST

This invention was made with United States Government support under Contract No. MDA 972-97-C0021 (Defense Advanced Research Project Agency, Biological Warfare Defense). The Government has certain rights in the invention.

FIELD OF THE INVENTION

This invention relates to methods for the detection of biological agents, especially biological warfare agents, using a spore-specific phosphorescence approach. More specifically, the methods of this invention allow the detection of the spores of biological warfare agents such as *Bacillus anthracis* and *Clostridium botulinum* at very high sensitivity (generally at levels of about 500 to 1000 spores or even lower) combined with high selectivity and ease of use. The methods of the present invention are especially adapted for use in the field (e.g., in terrorist or combat scenarios) by personnel at risk of exposure to such agents. A simple, single-person, hand-held or worn biological detector for field use is provided.

BACKGROUND OF THE INVENTION

Weapons of mass destruction are, unfortunately, a fact of life as we approach the 21$^{st}$ Century. Of grave concern are bacterial agents, such as *Bacillus anthracis* and *Clostridium botulinum*, that could be used by rogue or aggressor countries and/or international terrorists. Such biological agents could be easily dispersed in urban and/or battlefield areas using a multitude of delivery devices. Just the threat of such an attack can cause considerable harm to the threatened population or area as well as national security. Moreover, the risk of such threats and attacks will likely increase as it becomes increasingly easy to prepare, use, and/or deliver such biological agents anywhere in the world. Thus, highly sensitive and selective detection methods are vital to our national security both at home and abroad.

The detection methods currently available generally lack the desired sensitivity, selectivity, and/or speed for such bacterial agents as *Bacillus anthracis* and *Clostridium botulinum*. Currently available detection methods include, for example, PCR with fluorescence detection, fluorescent antibody staining techniques (FAST), partichrome analyzers, bioluminescence-based systems, electrochemiluminescence-based systems, and stimulated induced fluorescence techniques for on-site and remote detection. Some of these techniques (e.g., PCR with fluorescence detection, ELISA, and FAST), although having high specificity, have relatively low sensitivity (minimum of $10^4$ to $10^6$ spores for detection) and are time consuming (generally requiring 0.5 to 6 hours for results). See, e.g., Redkar et al., "Rapid Detection of Select Pathogenic Bacteria by Real Time PCR," Abstract, Scientific Conference on Chemical and Biological Defense Research, Aberdeen Proving Ground (1998); Ibrahim, "Detection of Biological Agents Using Probe-Based PCR Assay," Abstract, Scientific. Conference on Chemical and Biological Defense Research, Aberdeen Proving Ground (1998); Gatto-Menking et al., "Rapid Post PCR Protection Using IGEN's Origen Analyzer," Abstract, Scientific Conference on Chemical and Biological Defense Research, Aberdeen Proving Ground (1998); Bruno et al., "Development of Selex DNA Aptamers for the Detection of Anthrax Spores," Abstract, Scientific Conference on Chemical and Biological Defense Research, Aberdeen Proving Ground (1998); and Nagata et al., "Development of Enzyme-linked Immunosorbent Assay (ELISA) to Anthrax for the Persian Gulf," Defense Information System Agency, ADA297350 (1995). Bioluminescence- and electrochemiluminescence-based systems, although having increased sensitivity (minimum of about 200 spores for detection) and being somewhat faster, suffer because of reduced specificity. See, e.g., Gatto-Menking et al., "Rapid Post PCR Protection Using IGEN's Origen Analyzer," Abstract, Scientific Conference on Chemical and Biological Defense Research, Aberdeen Proving Ground (1998); and Bartoszcze et al., "The Sensitivity of the Bioluminescence Method Regarding Microbiological Detection in Contaminated Water and on Surfaces," Abstract, Scientific Conference on Chemical and Biological Defense Research, Aberdeen Proving Ground (1998). Additionally, stimulated induced fluorescence methods have be used to detect or target the amino acid tryptophan. However, since tryptophan is common to most biological materials, techniques relying on its detection have very poor selectivity.

There remains, therefore, a need for simple detection methods and devices for bacterial agents such agents as *Bacillus anthracis* and *Clostridium botulinum*. Moreover, there remains a need for such detection methods and devices having high sensitivity and high selectivity and which can provide real-time data. There remains a need for such detection methods and devices which can be carried by personnel who may be exposed to such bacterial agents and provide warning so that protective measures can be taken to avoid or minimize exposure to such bacterial agents. There also remains a need for such detection methods and devices which have low rates of false positives. This invention provides such methods and devices for the detection of bacterial agents such as *Bacillus anthracis* and *Clostridium botulinum*. This invention also provides such methods and devices for the detection of viable spores of *Bacillus anthracis* and *Clostridium botulinum*. Moreover, these and other advantages and benefits of the present methods and devices will be apparent from a consideration of the present specification.

SUMMARY OF THE INVENTION

This invention provides methods and devices for the detection of bacterial agents such as *Bacillus anthracis* and *Clostridium botulinum*, including viable spores *Bacillus anthracis* and *Clostridium botulinum*, with high sensitivity and selectivity. More specifically, the present invention provides a phosphorescence-based detection system using chelated lanthanides (e.g, Eu(III), Tb(III), and Sm(III)) as the sensor component to detect various spore-specific small organic molecules (e.g., dipicolinic acid, diaminopimelic acid, n-acetlymuramic acid, and the like). By careful selection of the polydendate chelating agent or ligand attached to the lanthanide, sensor compounds having stability over a wide range of pH values can be obtained. This pH stability allows for the use of optimum pH values for specific "target" compounds associated with, and specific for, the bacterial spores. Thus, this stability allows for both high specificity and selectivity in the methods of this invention. Examples of suitable and preferred sensor systems include N-(2-hydroxyethyl)-ethylenediaminetriacetic acid (HEDTA) and/or N-(2-hydroxyethyl)iminodiacetic acid (HEIDA) bound with europium (III) and/or terbium (III). The chelated lanthanides (e.g., Eu(III)-HEDTA, Tb(III)-HEDTA, Eu(III)-HEIDA) and Tb(III)-HEIDA) react with the spore-specific "target" molecules to form a characteristically phosphorescent product which can then be detected and, if desired, quantified.

One object of the present invention is a device for the detection of biological warfare agent spores, said device comprising (1) a matrix with a chelated lanthanide compound immobilized therein, wherein the chelated lanthanide compound can react with spore-specific target compounds derived from the biological warfare agent spores to produce a reaction product that is capable of producing a characteristic phosphorescent emission; (2) a means for exciting the reaction compound to produce the characteristic phosphorescent emission; and (3) a means for detecting the characteristic phosphorescent emission; wherein the spore-specific target compounds are selected from the group consisting of dipicolinic acid, diaminopimelic acid, n-acetylmuramic acid, sulfolactic acid, and phosphoglyceric acid. Preferably, the chelated lanthanide compounds are N-(2-hydroxyethyl) ethylenediaminetriacetic acid or N-(2-hydroxyethyl) iminodiacetic acid chelates of the lanthanide ions europium (III), terbium (III), or samarium (III) wherein the lanthanide ions are partially chelated and have at least two coordination sites available for reaction with the spore-specific target compounds. More preferred are the europium (III) and/or terbium (III) chelates. Preferred target compounds include dipicolinic acid, diaminopimelic acid, and n-acetylmuramic acid. Preferably, the device also has an alarm mechanism which is activated if the characteristic phosphorescent emission is detected.

Another object of the present invention is a method for the detection of biological warfare agent spores in a sample, said method comprising: (1) providing a matrix containing an immobilized partially chelated lanthanide compound which can react with spore-specific target compounds derived from the biological warfare agent spores to produce a reaction product that is capable of producing a characteristic phosphorescent emission; (2) contacting at least a portion of the matrix with the sample; (3) irradiating the portion of the matrix with exciting radiation to produce the characteristic phosphorescent emission; and (4) detecting the characteristic phosphorescent emission; wherein the detection of the characteristic phosphorescent emission indicates the presence of biological warfare agent spores in the sample. Preferably, the partially chelated lanthanide compounds are N-(2-hydroxyethyl)-ethylenediaminetriacetic acid or N-hydroxyethyliminodiacetic acid chelates of the lanthanide ions europium (III), terbium (III), or samarium (III) wherein the lanthanide ions have at least two coordination sites available for reaction with the spore-specific target compounds. More preferred are the europium (III) and/or terbium (III) chelates. Preferably, the method also includes the activation of an alarm if the characteristic phosphorescent emission is detected.

These and other objectives and advantages of the present invention will be apparent to those of ordinary skill in the art upon consideration of the present specification and appended claims.

DESCRIPTION OF THE PREFERRED EMBODIMENTS

Figure 1:
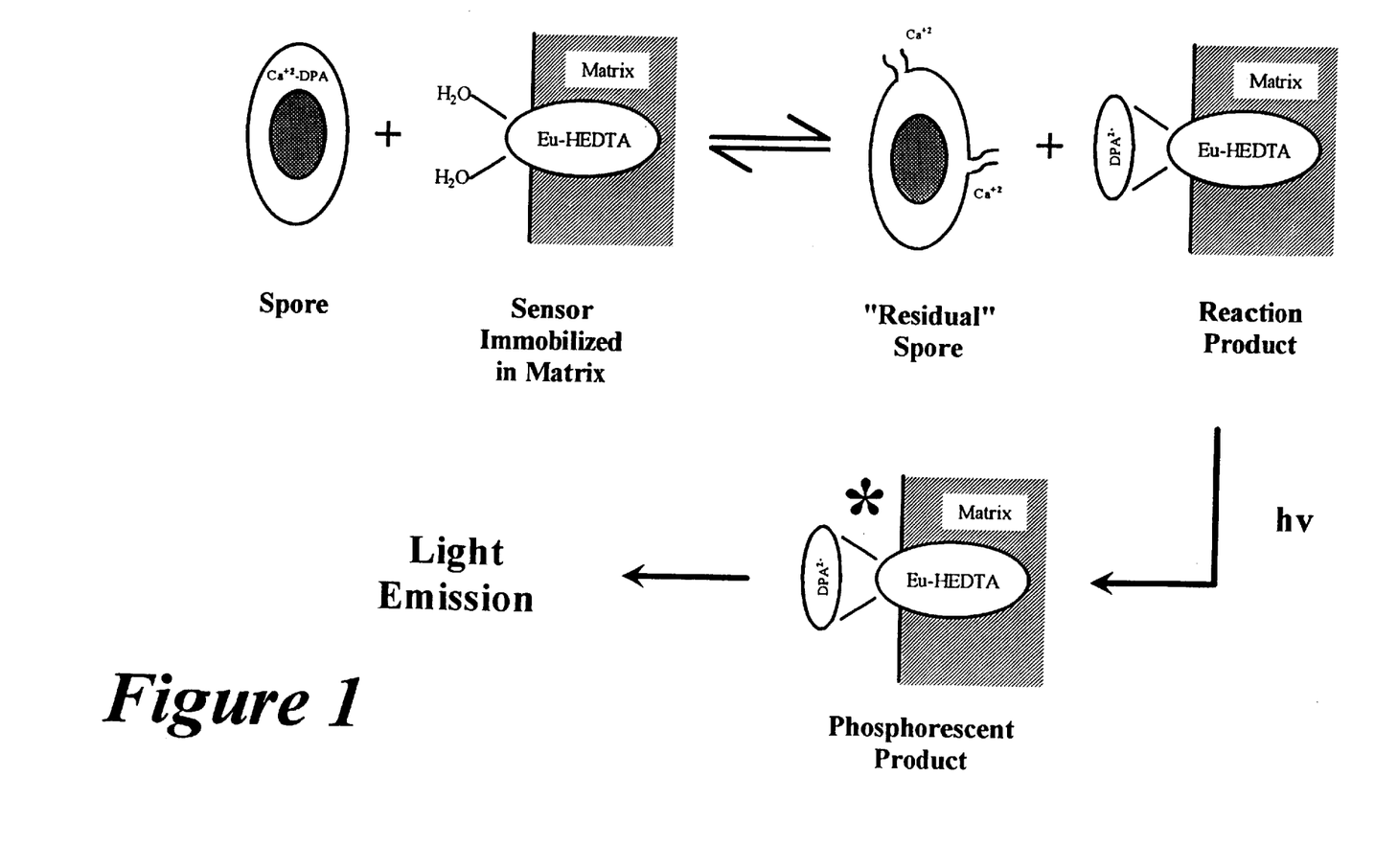
FIG. 1 provides an idealized reaction scheme illustrating the formation of a phosphorescent reaction product resulting from the interaction of a chelated europium sensor compound with bacterial spores.

The present invention provide methods and devices for the detection of biological warfare agents, especially *Bacillus anthracis* and *Clostridium botulinum*, using spore-specific phosphorescence. More specifically, the present invention provide methods and devices for the detection of spores of *Bacillus anthracis* and *Clostridium botulinum* using spore-specific. phosphorescence. The present methods and devices are based on the reaction of specific spore-derived small target molecules with sensor compounds to produce a reaction products having unique phosphorescence characteristics. The general reaction scheme can be illustrated by the following equations:

$$\text{Sensor} + \text{Target-Spore} \leftrightarrows \text{Reaction Product} + \text{Residual Spore}$$

and $$\text{Reaction Product} + h\nu_1 \rightarrow \text{Phosphorescent Product} \rightarrow \text{Light Emission} (h\nu_2)$$

where the exciting frequence $v_1$, is typically in the range of about 270 to 280 nm and emission frequency is typically in the range of about 500 to 650 nm. The phosphorescent reaction product, if formed, indicates the presence of spores of the biological warfare agent. The phosphorescent reaction product (i.e., sensor-target moiety) should have a characteristic phosphorescence for detection purposes. This reaction scheme is also illustrated in FIG. 1 using an immobilized Eu-HEDTA sensor and a *Bacillus anthracis* spore having dipicolinic acid (DPA) in or associated with its cortex. As can be seen in FIG. 1, DPA is chelated to europium to form the phosphorescent product (i.e., Eu(III)-HEDTA-DPA chelate). The Eu(III)-HEDTA-DPA chelate, when excited at the appropriate wavelength (i.e., about 271 nm), will exhibit a characteristic phosphorescence emission. Generally, the target compounds are more readily released from spores at acidic pHs (generally about 2 to about 4); thus, sampling is preferably carried out at low pH values. To obtain high phosphorescence sensitivity, however, it is preferred that the matrix containing the sensor compounds, once chelated with the target compounds during the sampling period, is adjusted to basic conditions (generally about 10–12). Thus, it is generally preferred that the methods and devices of this invention have the ability to adjust the pH form relative low values during sampling to maximize release of target compounds and then to relative high values to maximize the phosphorescent reactions. The sensor compounds of the present invention are stable over this relatively broad range of pH values.

Suitable sensor compounds are chelated lanthanides wherein at least one, and preferably at least two, coordination sites on the lanthanide ion are available for reaction with the target compounds. Suitable lanthanides include, for example, europium, terbium, samarium, and mixtures thereof. Generally the preferred lanthanides are Eu(III) and Tb(III). Non-spore related bidentate or other multi-dentate chelating agents or ligands can be used to stabilize the lanthanide ions. Examples of preferred ligands, each having four or more potential binding sites for the lanthanide metal ions, include N-(2-hydroxyethyl)ethylened iaminetriacetic acid (H EDTA), N-(2-hydroxyethyl)iminodiacetic acid (HEIDA), and mixtures thereof. Preferred chelated sensor compounds include Eu(III)-(HEDTA)$_x$, Eu(III)-(HEIDA)$_x$, Tb(III)-(HEDTA)$_x$, Tb(III)-(HEIDA)$_x$, Sm(III)-(HEDTA)$_x$, and Sm(III)-(HEIDA)$_x$, where x is from 1 to 2, inclusive. Generally, sensor compounds where x is 2 are preferred. Especially preferred chelated sensor compounds include Eu-(HEDTA)$_2$, Eu(III)-(HEIDA)$_2$, Tb(III)-(HEDTA)$_2$, and Tb(III)-(HEIDA)$_2$ where the molar ratio of lanthanide to ligand is 1:2. Compounds having 1:2 ratio of lanthanide to chelate still have at least two potential binding sites available since, because of steric hindrance, the lanthanide is only partially chelated. Of course, other ligands may be used so long as they can immobilize and stabilize the sensor compound and the sensor compound, when reacted with target compounds from the spore, provides the necessary phosphorescent complex. Other such ligands include, for example, nitrilotriacetic acid, iminodiacetic acid, ethylenediaminetetraacetic acid, and the like. As noted above, the release of target compounds from spores is enhanced at low pH values while the phosphorescence reactions are enhanced at high pH values. Thus, it is preferred that the lanthanide chelate sensor compounds are stable over this broad pH range.

The lanthanide chelate sensor compounds of this invention must have at least one coordination site open or available for binding with the target compounds from the spores. Preferably, the lanthanide chelate sensor compounds have at least two coordination sites open or available for binding with the target compounds from the spores. Generally, it is preferred that the lanthanide chelate sensor compounds have two coordination sites available for binding. General idealized structures of such lanthanide chelate sensor compounds having two and four coordination sites, respectively, available for binding with target compounds are as follows:

where Ln is the lanthanide ion and dark curved lines represent a quadra-dentate and a bidentate ligand, respectively. Examples of such multi-dentate ligands include HEDTA and HEIDA:

HEDTA

HEIDA where dotted lines represent potential binding sites. Of course, as those skilled in the art will realize, such multidentate ligands may not use all of their binding sites to attach to the lanthanide ions. Indeed, some of these binding sites will remain unbound due steric constraints.

The target molecules used for the methods and devices of this invention are spore-specific and are generally relatively small molecules. Suitable target molecules, derived from the spores of *Bacillus anthracis* and *Clostridium botulinum*, include dipicolinic acid, diaminopimelic acid, n-acetylmuramic acid, sulfolactic acid, and phosphoglyceric acid. Preferred target molecules include dipicolinic acid, diaminopimelic acid, and n-acetylmuramic acid. Dipicolinic acid is a significant component of *Bacillus anthracis*; diaminopimelic acid and n-acetylmuramic acid are significant components of *Clostridium botulinum*. Moreover, n-acetylmuramic acid is normally associated with the spore mucopeptide. Structures of the target compounds dipicolinic acid, diaminopimelic acid, showing their potential binding sites to the lanthanide ion, are as follows:

Diamiopimelic Acid (DAP)

Dipicolinic Acid (DPA)

The phosphorescence exciting and emission wavelengths of the sensor compound will vary depending on the specific lanthanide and ligand used (i.e., the specific sensor system) and the target species. For example, the maximum excitation phosphorescence is observed near 270 nm for the Eu(III) and Tb(III) sensor compounds bound to dipicolinic acid. The maximum phosphorescence emission is at about 545 nm for Tb(III) sensor compounds and at about 625 nm for Eu(III) sensor compounds. Generally, sensor compounds having a molar ratio of lanthanide to ligand between about 1 to 1 and about 1 to 2 are preferred. More preferred molar ratios for the lanthanide and ligand are about 1 to 2. Using appropriate sensor compounds, the phosphorescence emission characteristics of the sensor-target compound reaction product can be varied dramatically.

In practice, the sensor compounds are preferably contained in an acivated matrix. Suitable matrices include, for example, organic polymer gels (e.g., agarose), sol-gels, or films, inert inorganic oxides, filter papers, and cellulose or other fiberous materials. Although the matrix is preferably porous (i.e., air samples can be readily drawn or passed through the matrix), impervious films or laminates may be used if coated with a layer containing the sensor compounds. Generally, near real time monitoring (i.e., approximately 5 to 15 minutes or less cycling times) can be achieved with the methods and devices of this invention. Sensitivity will depend on sampling rate, sampling time, and the detection limit of the detector used. Detection limits of less than about 500 spores (colony forming units) with near real time sampling are possible with this invention.

The present methods and devices are designed to detect spores of bacterial warfare agents such as *Bacillus anthracis* and *Clostridium botulinum*, using spore-specific phosphorescence. If desired, quantitative data can be obtained with the methods of the present invention. Generally the methods and devices of the present invention can be adapted to various types of samples, including, for example, gas (e.g., air), liquid, aerosols, and solid samples. As those of ordinary art will realize, the specific sensor devices illustrated in the various figures can be modified depending on the specific type of sample to be tested. Although the designs in FIGS. 2–5 are generally designed for gas or aerosol sampling, they could easily be modified to accommodate other sampling procedures. For example, these devices could easily be modified to accept liquid samples; such devices would be especially suitable for automatically monitoring water from reservoirs and/or water treatment plants.

Figure 2:
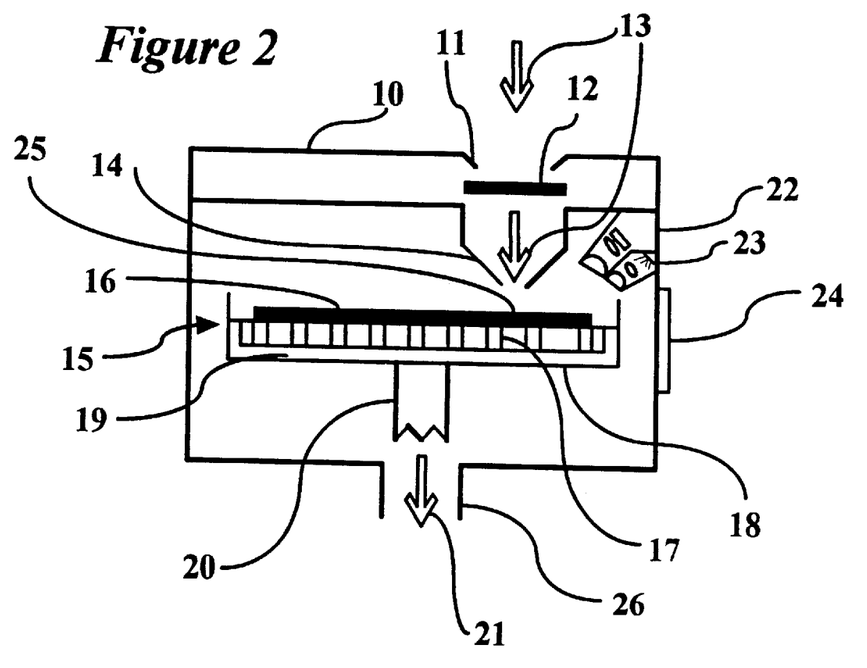
FIG. 2 illustrates a device for the detection of spores of biological warfare agents such as *Bacillus anthracis* and *Clostridium botulinum*.
Figure 3:
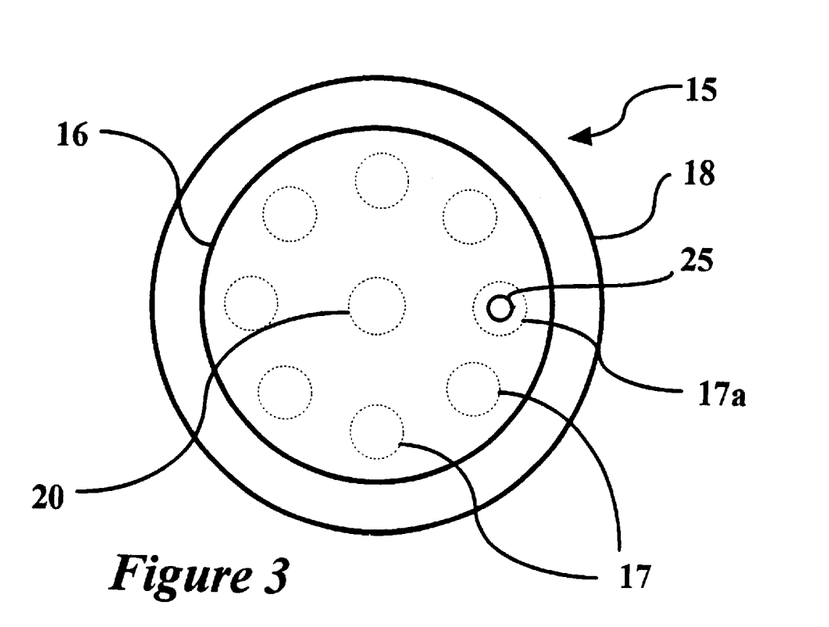
FIG. 3 illustrates the matrix holding assembly of the device in FIG. 1 in more detail.
Figure 4:
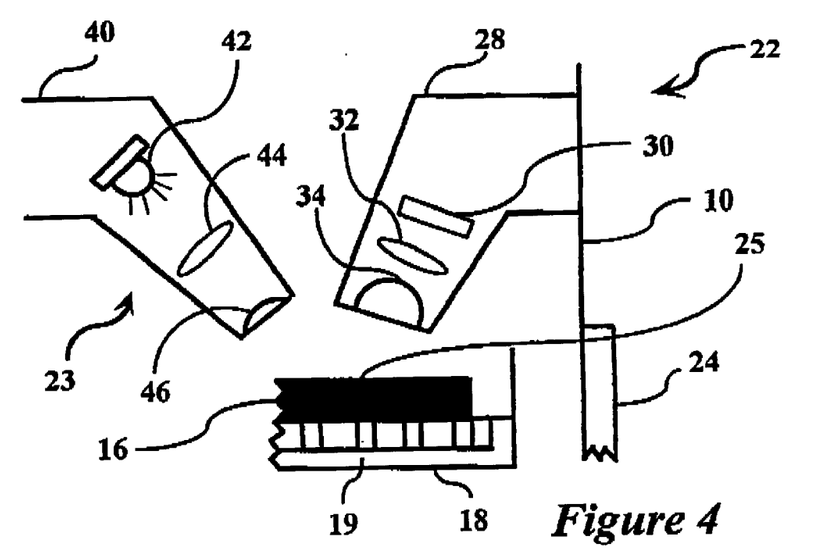
FIG. 4 illustrates the exciting and the detection systems of the device in FIG. 1 in more detail.

Sensors devices containing the above-described sensor compounds are provided in FIGS. 2 to 5. The sensor device illustrated in FIGS. 2 to 4 is generally designed for placement in a fixed location such as, for example, around the perimeter of a secured area. The device is contained in an appropriate housing 10 with a sample entry port 11. Air flow through entry port 11 is illustrated by large arrows 13. Upon entering port 11, the sample will first contact a screen or filter 12 to remove larger particles or dust in the general vicinity of the sampler. Although not shown, the device may also have a top or chimney-type cap placed directly above the entry port 11 and raised above the outside of housing 10 to help prevent settling dust particles from entering the system; the air would pass around the cap to enter port 14. Indeed, a screen material (also not shown) could be placed between the top cap and the container to further reject relatively large particles (e.g., dirt clots thrown up by passing vehicles). Other external modifications (e.g., directional windvanes or size selective screens) can be made with regard to the inlet geometry to reduce or minimize background interference.

After passing the filter 12, the air flow is directed through the focusing opening or impactor jet 14 in order to contact sampling area or portion 25 of matrix 16 housed in matrix holding assembly 15 (presented in more detail in FIG. 3). The matrix holding assembly 15 includes a porous matrix 16 containing the lanthanide sensor compound which rests upon, and is supported by, rotating plate 18 mounted on rotating shaft 20. The plate 18 has a plurality of openings 17 and a single sample area or opening 17a (which can be in the form of screens to better support porous matrix) which align, when rotated into the proper position with focusing opening 14 (best seen in FIG. 3). (The opening 17a is the one directly under the focusing device 14; as the porous matrix 16 is rotated, the new opening underneath the focusing opening 14 will become opening 17a). Air directed through focusing opening 14 impinges on the portion 25 of the porous matrix 16 directly underneath focusing opening 14 and passes through the porous matrix 16, through the associated opening 17a, and then out exit 16 (as indicated by arrow 21). If desired, the flow of air can be assisted using a vacuum pump or other air moving equipment (not shown) attached to exit port 26.

Channel or reservoir 19 of matrix holding assembly 15 can contain various solvents and/or reagents to maintain the porous matrix 16 in the appropriate condition to obtain the desired high selectivity and sensitivity. Preferably, two reservoirs (not shown) are provided. Preferably, the first reservoir contains an acidic aqueous solution having a pH of about 2 to 4 and other conditioning reagents; and the second, a basic aqueous solution having a pH of about 10 to 11. The acid solution will generally be used or activated during sample collection as low pH facilitates the release of target compounds such as DPA and DAP from the bacterial spores. The basic solution will generally be used or activated after a predetermined sampling time in order to facilitate production of the phosphorescent product. The matrix 16 can be "wetted" with the reagents contained in reservoir or reservoirs using, for example, wicking action. Alternatively, such reagents could, for example, be contained in a separate containers or reservoirs (not shown) in housing 10 and then sprayed on the sampling area just prior to collection of the sample. Or, in a still further alternative, such reagents could be contained within the porous matrix 16 itself. In an even further alternative, the plate upon which the matrix 16 could itself be porous thereby allowing the necessary reagents to enter into the matrix directly. Spores in the air sample will react with the sensor compound contained in porous matrix 16 to form the phosphorescent reaction product.

The phosphorescent emission of the reaction product, if formed (i.e., if spores are contained in the air sample), can be detected using light source unit 23 and detector unit 22. Light source unit 23 provides the light energy to form the phosphorescent product from the target compound-chelated lanthanide reaction product and detector unit 22 provides the means to detect the light emission from the phosphorescent product (see FIG. 1). As shown in more detail in FIG. 4, light source unit 23 is contained in housing 40 and contains a fixed focus lens 46, wavelength or bandpass filter 44, and light source 42. The light source unit 23 provides the exciting energy to generate the phosphorescent reaction product. One or more bandpass filters 44 can be used to filter out non-relevant wavelengths, and especially wavelengths at or near the emission frequencies expected to be given off by the phosphorescent reaction product. Light source 42 can be any light source or lamp that can fit within the device and which provides light at the required frequency (i.e., at the exciting frequency of the sensor compound). One such preferred light source is a deuterium lamp (FiberLight) from Heraeus Amersil Inc. (Duluth, Ga.) which can, when used with the appropriate filters 44, provide the appropriate excitation energy (i.e., about 270 to 280 nm) for the sensor-spore reaction product. The detector unit 22 is contained in housing 28 and contains a fixed-focused lens 34, wavelength or bandpass filter 32, and detector 30. One or more bandpass filters could be used to filter out non-relevant wavelengths (i.e., wavelengths not specific to the phosphorescent reaction products expected when spores of the biological warfare agents are present). Detector 30 is preferably one or more photocells or photomultipliers.

Moreover, the photocell could be coupled to a capacitor to require a minium voltage in a predetermined time period. Such a system would be expected to reduce the number of false positives and, therefore, minimize the problem associated with the "boy who cried wolf too often" syndrom. Human nature being as it is, the higher the rate of false positives, the greater risk of personnel delaying action when an alarm sounds or even ignoring the warning entirely; such delay in the case of an actual attack or release could be fatal. Thus, warning systems in which the number of false positives are significantly reduced without impairing the desired high sensitivity and selectivity are preferred In addition, a plurality of such detectors units 22 can be used where each such detector unit 22 is designed to detect a specific characteristic phosphorescence emission. Such a multi-detector system would preferably be used with several different sensors compounds (with each having its characteristic phosphorescence emission). Likewise, a series of detector/matrix combinations could be combined to obtain even more detailed information; in same cases, this combination may be preferred since each separate system could be individually optimized for maximum sensitivity and/or selectivity.

As suggested in FIGS. 2 and 4, the light unit 23 and detector unit 30 can be located at different locations within the housing 10. Although not shown, one or both of the light unit 23 or detector unit 22 could incorporate optical fibers, thus allowing them to be located at locations within the housing 10 which are not in direct sight lines with sampling portion 25 of matrix 16. Such an optical fiber could be used to provide the required exciting light energy from the light unit 23 to the sensor compound within area 25 on the porous matrix 16. Likewise, such an optical fiber could be used to collect the light emission from the phosphorescent product in the same area 25 and provide it to the detector unit 22. Using such optical fibers, the light unit 23 and/or detector unit 22 could be located in portions of housing 10 remote from porous matrix 16. Such optical fibers could easily be focused on the area 25 of the porous matrix 16 and could allow a higher density of sampling sites on porous matrix 16. As noted, the use of such optical fibers would also reduce "crowding" around the area in which the same impinges on area 25 of the porous matrix. Moreover, the use of such optical fibers would allow construction of warning devices having two or more matrixes containing different lanthanide sensor compounds to provide even greater warning capabilities.

If spores are detected, an appropriate warning or signal should be generated. Such signaling or warning devices (not shown) are well known in the art. For example, the detector 30 could be used to activate a visual and/or auditory warning. The detector 30 could also be used to activate a radio signal to activate a remote warning signal or device. Such a radio activation system could be used to good effect, for example, for remote warning systems. Indeed, such remote sensors mounted around the perimeter of an area could provide early warning of an attack using (or accidental release of) biological warfare agents; if the various sensors are equipped with detectors operating at different frequencies, directional information regarding the attack or release could also be generated.

After a sampling cycle is complete, the matrix holding assembly 15 can be rotated and indexed to a new position to expose a new (i.e., fresh or unexposed) area of the matrix 16 to the flow of air. Although only eight sampling areas or positions 17 are shown in FIG. 3, those skilled in the art will realize that many more such sampling sites (as well as different shaped sampling sites) could be used. If desired, a protective cover (not shown) could be used to cover and/or protect portions of the matrix 16 that are not currently being used for detection (i.e., all areas of matrix 16 except the portion 25 under focusing device 14). Such a protective, non-rotating cover could be fitted over assembly 15 such that only the sampling area is exposed to the air sample. Such a protective cover must allow, of course, monitoring of the sampling area using detector 22. Once all appropriate areas of the matrix 16 have been used, the matrix can be removed and a new matrix inserted using access door 24. Generally, in high risk situations, the specific sampling areas 17 of matrix 16 would only be used once before replacement. In other, lower risk cases, the specific sampling areas 17 may be used more than once (i.e., more than one complete rotation of assemble 15). Replacement protocols could be based on number of exposures of the sample areas or on time of use. Of course, once the matrix 16 has been exposed to bacterial spores (i.e., such spores have been detected), the matrix 16 should be replaced as soon as conditions warrant.

As detailed above, a porous matrix 16 mounted in the matrix holding assembly 15 can be used. Of course, other configurations or designs may be used. For example, the matrix 16 could be a non-porous plastic film with the appropriate reagents, including the lanthanide sensor compounds, coated thereon. In such an embodiment, the air stream or flow 13 would be directed to an appropriate area of the film to contact the reagents; the air flow would then pass around assembly 15 and then through exit 26. In such a system, the openings 17 and 17a would not be needed in the matrix holding assembly 15.

Figure 5:
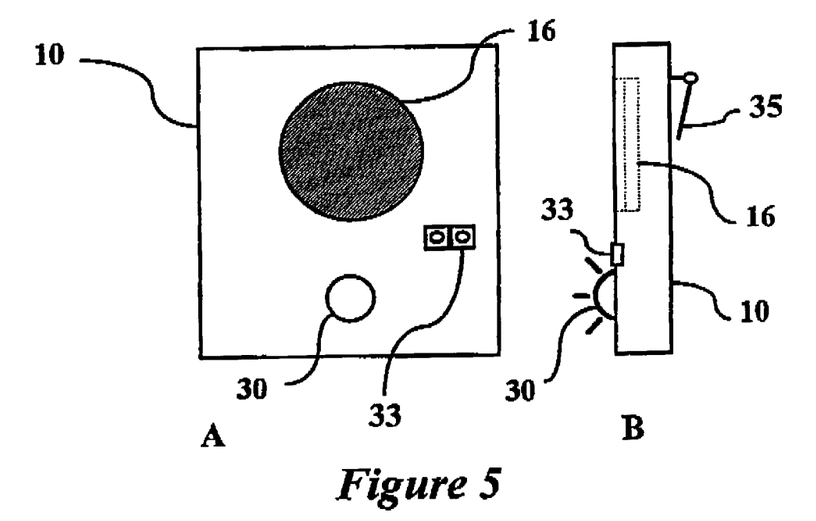
FIG. 5 illustrates another device for the detection of spores of biological warfare agents such as *Bacillus anthracis* and *Clostridium botulinum* for personal use in the field. Panels A and B provide the front and side views, respectively.

Another embodiment of the sensor device of this invention is shown in FIG. 5. This embodiment could be used by an individual in the field. The sensor housing 10 has a clip or other fastener 35 for attachment to, for example, a shirt pocket, other clothing, or equipment. The porous matrix 16 containing the lanthanide sensor compounds is exposed to the air (an appropriate porous film, not shown, can be mounted over the matrix 16 for protection if desired). Using appropriate detectors (similar to those used in sensor 22 above), a warning device 30 can be activated if spores are detected. Warning device 30 can be, for example, a light, buzzer, or the like. Of course, sensors designed for combat type situations would preferably have a warning device that would not be observable by opposing forces; in such cases, a vibrating warning signal or an ear plug device could be used. In addition, such a personal warning device could also contain a radio signal, beacon, or other such device to pass the warning onto others, thus, providing them even earlier warning (i.e., before their personal devices are even exposed to the bacterial spores).

Preferably, the sensor is equipped with at least dual-selectivity and sensitivity settings 33. By providing at least two different lanthanide sensor compounds which, when exposed to the appropriate spores, form different phosphorescence reaction products emitting at different frequencies, the number of false positives (and, again, the "boy who cried wolf too often" syndrom) can be substantially reduced. During normal operational activities (i.e., where the risk of exposure is low), the device could be set to require at least two positive signals (i.e., from each of at least two different emission frequencies) to activate the alarm. However, in circumstances where the risk of exposure is high (e.g., where opposing forces have used biological warfare agents in the past and/or where intelligence indicates that their use is a real possibility), the device could be set to activate the alarm when any one positive signal is detected. In former case, the incident of false positives will be reduced; in the later case, sensitivity would be maximized. Although not shown, such a dual activation system could be implemented in the sensors illustrated in FIG. 2. In the case of such remote sensors, the switch to high sensitivity could be implemented from an appropriate radio or other signal from command posts or headquarters when conditions warrant or automatically when any one sensor (operating at the lower sensitivity) detects exposure to such biological warfare agents.

The sensor devices of the present invention can be powered by any conventional energy source. For example, the present sensor can use conventional alternating current, when available, with, as appropriate, step-down transformers, or self contained batteries, photovoltaic systems, and the like as well as combinations thereof. For example, a sensor directly wired or a sensor equipped with a photovoltaic system could also, and in many cases preferably would, be equipped with a back-up battery system. The electronic systems, including timing circuits, transmitters, and the like used to implement the present sensors are generally commercially available and well known to those in the art and, thus, do not need to be describe here.

That which is claimed is:

1. A non-invasive field use device for detection of biological warfare agent spores, said device comprising:
   an activated matrix comprising:
      a matrix, activated by immobilizing therein, a multidentate chelated lanthanide compound stabilized by a predetermined multidentate chelating ligand attached thereto, wherein the multidentate chelated lanthanide compound reacts optimally in a pH range of approximately 10–12 with spore-specific target compounds derived from the biological warfare agent spores to produce a reaction product that, upon being excited with selected UV-radiation, produces a characteristic phosphorescent emission;
   a first unit to excite the reaction product to produce the characteristic phosphorescent emission; and
   a second unit to detect the characteristic phosphorescent emission,
   wherein the spore-specific target compounds are selected from the group consisting of dipicolinic acid, diaminopimelic acid, n-acetylmuramic acid, sulfolactic acid, and phosphoglyceric acid.

2. The device as defined in claim 1,
   wherein biological warfare agent spores are from *Bacillus anthracis* or *Clostridium botulinum*;
   wherein the spore-specific target compounds are selected from the group consisting of dipicolinic acid, diaminopimelic acid, and n-acetylmuramic acid; and
   wherein the device detects biological warfare agent spores in near real time.

3. The device as defined in claim 2, wherein the predetermined multidentate chelating ligand stabilizing the lanthanide compound is a N-(2-hydroxyethyl) ethylenediaminetriacetic acid or a N-(2-hydroxyethyl)-iminodiacetic acid, wherein the chelated lanthanide compound is a N-(2-hydroxyethyl)ethylenediaminetriacetic acid chelate of europium (III), terbium (III), or samarium (III) or a N-(2-hydroxyethyl)-iminodiacetic acid chelate of europium (III), terbium (III), or samarium (III), and wherein the chelated lanthanide compound has at least two coordination sites available for reaction with the spore-specific target compounds.

4. The device as defined in claim 2, wherein the chelated lanthanide compound is a europium (III) chelate or a terbium (III) chelate.

5. The device as defined in claim 3, wherein the chelated lanthanide compound contains europium (III) or terbium (III).

6. The device as defined in claim 2, further comprising an alarm system which is activated if the characteristic phosphorescent emission is detected.

7. The device as defined in claim 5, further comprising an alarm system which is activated if the characteristic phosphorescent emission is detected.

8. The device as defined in claim 2,
   wherein the activated matrix contains at least two chelated lanthanide compounds immobilized therein,
   wherein each of the chelated lanthanide compounds reacts with spore-specific target compounds derived from the biological warfare agent spores to produce at least two separate reaction products that, upon being excited, produce at least two different characteristic phosphorescence emissions; and
   wherein the device further contains an alarm system with at least first and second operator-selected operational modes, where the alarm system is activated in the first operational mode when either of the two different characteristic phosphorescent emissions are detected and where the alarm system is activated in the second operational mode when both of the two different characteristic phosphorescent emissions are detected.

9. The device as defined in claim 5,
   wherein the activated matrix contains at least one of the two chelated lanthanide compounds immobilized therein,
   wherein the chelated lanthanide compound/compounds reacts/react with spore-specific target compounds derived from the biological warfare agent spores to produce at least one/two separate reaction products that, upon being excited by the UV-radiation, produce at least one/two different characteristic phosphorescent emissions; and
   wherein the device further contains an alarm system with at least first and second operator-selected operational modes, where the alarm system is activated in the first operational mode when either of the two different characteristic phosphorescent emissions are detected and where the alarm system is activated in the second operational mode when both of the two different characteristic phosphorescent emissions are detected.

10. A method for non-invasive field use detection of biological warfare agent spores in a sample, said method comprising:
   providing an activated matrix comprising a matrix, activated by immobilizing therein a multidentate chelated lanthanide compound stabilized by a predetermined multidentate chelating ligand attached thereto, wherein the multidentate chelated lanthanide compound reacts optimally in a pH range of approximately 10–12 with spore-specific target compounds derived from the biological warfare agent spores to produce a reaction product that, upon being irradiated with exciting radiation, produces a characteristic phosphorescent emission;
   contacting at least a portion of the activated matrix with the sample;
   irradiating the portion of the activated matrix with exciting radiation to produce the characteristic phosphorescent emission; and detecting the characteristic phosphorescent emission, wherein the detecting of the characteristic phosphorescent emission indicates that biological warfare agent spores are present in the sample.

11. The method as defined in claim 10, wherein biological warfare agent spores are derived from *Bacillus anthracis* or *Clostridium botulinum*, wherein the spore-specific target compounds are selected from the group consisting of dipicolinic acid, diaminopimelic acid, and n-acetylmuramic acid, and wherein the device detects biological warfare agent spores in near real time.

12. The method as defined in claim 10, wherein the predetermined multidentate chelating ligand stabilizing the lanthanide compound is a N-(2-hydroxyethyl) ethylenediaminetriacetic acid or a N-(2-hydroxyethyl)-iminodiacetic acid, wherein the chelated lanthanide compound is a N-(2-hydroxyethyl)ethylenediaminetriacetic acid chelate of europium (III), terbium (III), or samarium (III) or a N-(2-hydroxyethyl)iminodiacetic acid chelate of europium (III), terbium (III), or samarium (III), and wherein the chelated lanthanide compound has at least two coordination sites available for reaction with the spore-specific target compounds.

13. The method as defined in claim 10, wherein the chelated lanthanide compound is a europium (III) chelate or a terbium (III) chelate.

14. The method as defined in claim 12, wherein the chelated lanthanide compound contains europium (III) or terbium (III).

15. The method as defined in claim 10, further comprising activating an alarm if the characteristic phosphorescent emission is detected.

16. The method as defined in claim 14, further comprising activating an alarm if the characteristic phosphorescent emission is detected.

17. The method as defined in claim 10, wherein the activated matrix contains at least two chelated lanthanide compounds immobilized therein, wherein the chelated lanthanide compounds react with spore-specific target compounds derived from the biological warfare agent spores to produce at least two reaction products that, upon being excited, produce at least two different characteristic phosphorescent emissions; and providing an alarm system with at least a first and a second operator-selected operational modes, where the alarm system is activated in the first operational mode when either of the two different characteristic phosphorescent emissions are detected and where the alarm system is activated in the second operational mode when both of the two different characteristic phosphorescent emissions are detected.

18. The method as defined in claim 14, wherein the activated matrix contains at least two chelated lanthanide compounds immobilized therein, wherein the chelated lanthanide compounds react with spore-specific target compounds derived from the biological warfare agent spores to produce at least two reaction products that, upon being excited, produce at least two different characteristic phosphorescent emissions; and further including providing an alarm system with at least a first and a second operator-selected operational modes, where the alarm system is activated in the first operational mode when either of the two different characteristic phosphorescent emissions are detected and where the alarm system is activated in the second operational mode when both of the two different characteristic phosphorescent emissions are detected.

19. The method of claim 10, wherein before the contacting, the sample is brought to an acidic pH, and after the contacting, the pH surrounding the activated matrix is brought to an alkaline pH.

20. The method of claim 10, wherein before the contacting, the sample is brought to a pH of about 2 to about 4, and after the contacting, the pH surrounding the activated matrix is brought to a pH of about 10 to about 12.

* * * * *